United States Patent [19]

Cotrel et al.

[11] Patent Number: 4,720,500
[45] Date of Patent: * Jan. 19, 1988

[54] N-1,8-NAPHTHYRIDIN-2-YL AMIDES USEFUL AS IMMUNOSTIMULANTS

[75] Inventors: Claude Cotrel, Paris; Claude Guyon, St-Maur-des-Fosses; Gerard Roussel, Soisy-sur-Seine; Gerard Taurand, Creteil, all of France

[73] Assignee: Rhone-Poulenc Sante, Courbevoie, France

[*] Notice: The portion of the term of this patent subsequent to Feb. 10, 2004 has been disclaimed.

[21] Appl. No.: 884,212

[22] Filed: Jul. 10, 1986

[30] Foreign Application Priority Data

Jul. 11, 1985 [FR] France .................. 85 10619
Jan. 16, 1986 [FR] France .................. 86 00555

[51] Int. Cl.⁴ .................. A61K 31/44; C07D 471/04
[52] U.S. Cl. .................. 514/300; 546/122
[58] Field of Search .................. 546/122; 514/300

[56] References Cited

U.S. PATENT DOCUMENTS

4,086,348 4/1978 Cotrel et al. .................. 546/122

*Primary Examiner*—Henry R. Jiles
*Assistant Examiner*—Bernard I. Dentz
*Attorney, Agent, or Firm*—Stevens, Davis, Miller & Mosher

[57] ABSTRACT

Amides of formula

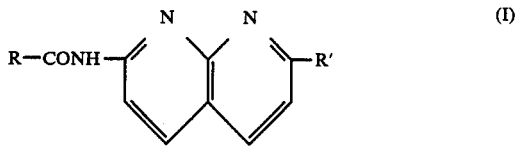

in which either R is 2-quinolyl, substituted phenyl (substituted by Br, 3-Cl, CF₃, alkyloxycarbonyl, 4-dialkylamino), dichlorophenyl, trialkyloxyphenyl, benzyl, styryl, benzoyl or anilino and R' is halogen, phenyl or anilino or R' is phenoxy or 4-chlorophenoxy when R is 2-quinolyl, substituted phenyl, trialkyloxyphenyl, benzyl or styryl or R' is 4-fluoro(or alkyloxy)phenyl when R is 4-trifluoromethyl (or dialkylamino)phenyl, or R' is 3-bromophenyl when R is anilino, or R is phenyl or alkyloxyphenyl and R' is phenyl, 4-chlorophenoxy, anilino or 1-pyrrolidinyl or R' is 2-(or 4-)chlorophenyl, 3-(or 4-)bromophenyl, 4-alkyloxyphenyl or 3,4-dichloro(or dibromo)phenyl when R is phenyl or R is 3-halophenyl and R' is 3-(or 4-)fluorophenyl, 3-(or 4-)bromophenyl, 4-chlorophenyl, 2-(or 3-)-alkyloxyphenyl, 3-alkylphenyl or 3,4-difluoro(dichloro or dibromo)phenyl, the straight-chain or branched alkyl radical containing 1 to 4 carbon atoms each, are useful as immunostimulant agents. The invention also provides processes for their preparation and pharmaceutical compositions containing them.

8 Claims, No Drawings

N-1,8-NAPHTHYRIDIN-2-YL AMIDES USEFUL AS IMMUNOSTIMULANTS

This invention relates to substituted pharmaceutically useful amides, their preparation and compositions containing them.

Benzamide derivatives of formula:

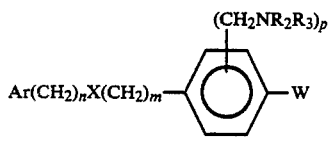

in which as an alternative X represents —NR$_1$CO—, stated to be useful as antiarrhythmics, have been described in PCT Patent Application No. 84/00489.

1,8-Naphthyridine derivatives of formula:

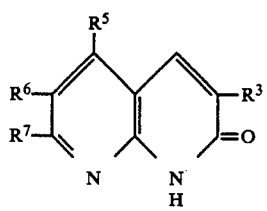

in which R$^6$ is —NH-alkanoyl have been described in Dutch Patent Application No. 73/05482 and U.S. Pat. No. 3,993,656. These compounds are stated to be useful as bronchodilators, periferal vasodilators and antihypertensives.

The present invention provides new substituded amides of the formula:

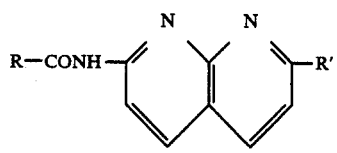

in which either (1) R represents 2-quinolyl, substituted phenyl (the substituent being bromine, chlorine in position-3, trifluoromethyl, alkyloxycarbonyl, or dialkylamino in position-4), dichlorophenyl, trialkyloxyphenyl, benzyl, styryl, benzoyl or anilino, and R' represents halogen, phenyl, anilino, or R' represents phenoxy or 4-chlorophenoxy when R is 2-quinolyl, substituted phenyl (the substituent being bromine, chlorine in position-3, trifluoromethyl, alkyloxycarbonyl, or dialkylamino in position-4), trialkyloxyphenyl, benzyl or styryl, or R' represents 4-fluorophenyl or 4-alkyloxyphenyl when R is 4-trifluoromethylphenyl or 4-dialkylaminophenyl, or R' represents 3-bromophenyl when R is anilino, or (2) R represents phenyl or alkyloxyphenyl and R' represents phenyl, 4-chlorophenoxy, anilino or 1-pyrrolidinyl, or R' represents 2-(or 4-)chlorophenyl, 3-(or 4-)bromophenyl, 4-alkyloxyphenyl or 3,4-dichloro(or dibromo)phenyl when R is phenyl, or (3) R represents phenyl substituted by halogen in position-3 and R' represents 3-(or 4-)fluorophenyl, 3-(or 4-)bromophenyl, 4-chlorophenyl, 2-(or 3-)alkyloxyphenyl, 3-alkylphenyl, or 3,4-difluoro(dichloro or dibromo)phenyl; the aforesaid alkyl radicals being straight-chain or branched and containining 1 to 4 carbon atoms each.

According to a feature of the invention, the compounds of formula (I) in which R is as defined above but is not anilino, and R' has the corresponding definition, are prepared by reacting an acid of the formula:

$$R\text{—COOH} \qquad (II)$$

in which R is as defined above, or a reactive derivative of this acid, with an amine of the formula:

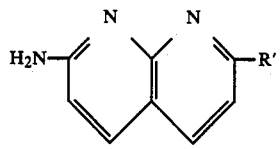

in which R' has the corresponding definition.

When an acid of formula (II) is employed, the reaction is carried out in the presence of a peptide condensing agent such as a carbodiimide (e.g. dicyclohexylcarbodiimide) or N,N'-carbonyldiimidazole or 2-ethoxy-1-ethoxycarbonyl-1,2-dihydroquinoline, in an organic solvent such as an ether (e.g. tetrahydrofuran, dioxane, glyme (ethylene glycol dimethyl ether), diglyme (diethylene glycol dimethyl ether), an amide (e.g. dimethylformamide), a nitrile (e.g. acetonitrile), a chlorinated solvent (e.g. methylene chloride, dichloroethane or chloroform) or an aromatic hydrocarbon (e.g. toluene), at a temperature of between 0° C. and the reflux temperature of the reaction mixture. The reaction is preferably carried out at about 20° C.

When a reactive derivative of the acid of formula (II) is employed, the reactive derivative may be, more particularly, the anhydride, a mixed anhydride, an acid halide or an ester (which may be an activated or nonactivated ester of the acid of formula (II)). The reaction is then carried out either in an organic medium, if appropriate in the presence of an acid acceptor such as a nitrogenous organic base (e.g. a trialkylamine, a pyridine, 1,8-diazabicyclo-(5.4.0)undec-7-ene or 1,5-diazabicyclo(4.3.0)non-5-ene), in a solvent as mentioned above, or a mixture of such solvents, at a temperature from 0° C. to the reflux temperature of the reaction mixture, or in a two phase aqueous organic medium in the presence of an alkali metal or alkaline-earth metal base (e.g. sodium hydroxide or potassium hydroxide) or of an alkali metal or alkaline-earth carbonate or bicarbonate, at a temperature of 0° to 40° C. It is also possible to operate without a solvent at the melting point of the reaction mixture. The reactive derivative of the acid may, if appropriate, be prepared in situ.

According to a further feature of the invention, the compounds of formula (I) in which the symbol R is an anilino radical, are prepared by reacting phenyl isocyanate with an amine of formula (III) in which R' represents halogen, phenyl, 2-bromophenyl or anilino.

The reaction is generally carried out in an organic solvent such as an ether (e.g. tetrahydrofuran or dioxane), a chlorinated solvent (e.g. methylene chloride, dichloroethane, or chloroform) or an amide (e.g. dimethylformamide), at a temperature of 0° to 80° C.

The acids of formula (II) may be prepared by applying the methods mentioned above or by analogy with these methods:

when R represents an alkyloxyphenyl radical according to the method described by S. M. Mac Elvain and T. P. Carney, J. Amer. Chem. Soc., 68, 2592 (1946);

when R represents an alkyloxycarbonylphenyl radical according to the methods described by K. G. Rutherford et al., J. Org. Chem., 28, 582 (1963), by B. H. Chase, J. Chem. Soc. 1334 (1963), or by S. Kasina, J. Pharm. Sci., 63, 1155 (1974);

when R is a trialkyloxyphenyl radical, according to the method described by E. Kasztreiner et al., Biochem. Pharmacology, 11, 651 (1962).

The amines of formula (III), in which R' represents phenoxy, 4-chlorophenoxy, anilino or 1-pyrrolidinyl, may be prepared from the corresponding amine of formula (III) in which R' is a halogen atom (preferably a chlorine atom), by reaction with phenol, 4-chlorophenol, aniline or pyrrolidine respectively.

When it is desired to obtain an amine of formula (III) in which R' is phenoxy or 4-chlorophenoxy, the reaction is carried out in a basic medium or in the presence of the corresponding alcoholate.

The reaction is generally carried out in the presence of a strong base (e.g. sodium hydroxide, potassium hydroxide, quaternary ammonium hydroxide, or sodium ethylate), at a temperature of 50° to 150° C., or in the presence of the corresponding alcoholate (e.g. sodium alcoholate), in a solvent such as an amide (e.g. dimethylformamide) or an ether (e.g. tetrahydrofuran or dimethoxyethane), or without a solvent, in the presence of an excess of hydroxylated derivative at a temperature between 70° C. and the reflux temperature of the reaction mixture.

When an alcoholate is employed, the latter may be obtained beforehand by reacting the alkali metal, e.g. sodium, with the alcohol at a temperature of 20° to 80° C., or by reacting the alkali metal hydride, e.g. sodium hydride, with the alcohol, at a temperature of between 0° to 20° C. in a solvent such as dimethylformamide, dimethoxyethane, or tetrahydrofuran. It is not necessary to isolate the alcoholate obtained in order to use it in the reaction which follows.

When it is desired to obtain an amine of formula (III) in which R' is anilino or 1-pyrrolidinyl, the reaction is carried out with or without a solvent at a temperature of 50° to 150° C. Dimethylformamide, dichloromethane or tetrahydrofuran are advantageously used as solvents.

The amines of formula (III) may also be prepared by applying the methods described in the Examples below or by applying the methods described by:

S. Carboni, Gazz. Chim. Italiana, 96, 1456 (1966); and

J. F. Harper and D. G. Wibberley, J. Chem. Soc., (C) 2985 (1971); or by methods analogous to these methods.

The amines of formula (III) in which R' is a substituted phenyl radical may be obtained by reacting a formate with the corresponding derivative of acetophenone, in the presence of sodium, followed by the reaction with 2,6-diaminopyridine in an acid medium.

The reaction is generally carried out in an anhydrous organic solvent such as an aromatic hydrocarbon (e.g. toluene) at a temperature of 10° to 40° C., and then at a temperature of 70° to 100° C.

When it is desired to obtain an amine of formula (III) in which R' is phenyl substituted by 2 fluorine atoms, the acetophenone derivative used as the starting material may be prepared according to the methods described by:

J. T. Minor et al., J. Org. Chem., 17, 1425 (1952),

M. G. Belsham et al., J. C. S. Perkin trans. II, 119 (1974) or

S. G. Malkevich et al., Plasliches Kie Massy, 4, 1 (1960) (Chem. Abs. 55 421i).

When it is desired to obtain an amine of formula (III) in which R' is phenyl substituted by 2 bromine atoms, the acetophenone derivative used as the starting material may be prepared according to the methods described by:

D. W. Mathieson et al., J. Chem. Soc., 1133 (1949) or

D. E. Pearson et al., J. Org. Chem., 23, 1412 (1958).

The new amides according to the present invention may be purified if necessary, by physical methods such as crystallization or chromatography.

The compounds of formula (I) have particularly valuable immunostimulant properties.

The immunostimulant activity has been demonstrated (1) in vitro at molar concentrations of $10^{-5}$ to $10^{-6}$ in the stimulation of the cytostatic activity of mouse peritoneal macrophages towards $P_{815}$ tumour cells using a technique based on that of M. I. C. Gyongyossi et al., Cell. Immunol., 45, 1 (1979); and (2) in vivo in mice, by a stimulation of the defensive reaction against *Klebsiella pneumoniae* infection which is observed at doses of 0.2 to 20 mg/kg i.p. using a technique based on that of M. A. Parant et al., Infect. Immun., 27, 826 (1980).

The immunostimulant activity of the new compounds makes it possible to use them as anti-infectious agents, especially for controlling microorganisms which have been resistant to generally used antibiotics.

Furthermore, the compounds of the invention have low toxicity. Their $LD_{50}$, when administered orally in mice, is either between 300 and 900 mg/kg, or greater than 900 mg/kg.

Of special value are the compounds of formula (I) in which either (1) R represents 2-quinolyl, 4-dialkylaminophenyl, dichlorophenyl, trialkyloxyphenyl, benzyl, styryl or benzoyl and R' represents chlorine or phenyl, or R' represents phenoxy when R is bromophenyl, or R' represents chlorine when R is bromophenyl, trifluoromethylphenyl or anilino, or R' represents 3-bromophenyl when R is anilino, or (2) R represents phenyl or alkyloxyphenyl and R' represents phenyl, 4-chlorophenoxy, anilino or 1-pyrrolidinyl, or R' represents 2-(or 4-)chlorophenyl, 3-(or 4-)bromophenyl, or 4-alkyloxyphenyl when R is phenyl, or (3) R represents phenyl substituted in the 3-position by halogen and R' represents 3-(or 4-)fluorophenyl, 3-(or 4-)bromophenyl, 4-chlorophenyl, 2-(or 3-)alkyloxyphenyl, 3-alkylphenyl or 3,4-difluoro(or dichloro or dibromo)phenyl, and the alkyl radicals mentioned above are straight-chain or branched and contain 1 to 4 carbon atoms each.

Among these products, the following are more particularly active:

N-(7-phenyl-1,8-naphthyridin-2-yl)-3-bromobenzamide;

N-(7-phenyl-1,8-naphthyridin-2-yl)-4-methoxybenzamide;

N-(7-pyrrolidinyl)-1,8-naphthyridin-2-yl)benzamide;

N-(7-(4-chlorophenyl)-1,8-naphthyridin-2-yl)-3-bromobenzamide; and

N-(7-(4-fluorophenyl)-1,8-naphthyridin-2-yl)-3-bromobenzamide.

The Examples which follow illustrate the present invention.

EXAMPLE 1

N,N'-Carbonyldiimidazole (2.4 g) is added to a solution of 3-bromobenzoic acid (3 g) in anhydrous tetrahydrofuran (50 cc). Gas is evolved immediately. The mixture is stirred for 2 hours at about 20° C., until the evolution of gas is complete. 2-Amino-7-phenyl-1,8-naphthyridine (2.4 g) is then added and the mixture is heated at the reflux temperature for 20 hours. The mixture is poured into distilled water (500 cc). The precipitate formed is separated by filtration, washed with water and air-dried.

The product obtained (3.8 g; m.p. 170°–175° C.) is dissolved in boiling acetonitrile (400 cc). After cooling for 4 hours at 4° C., the crystallized solid is separated by filtration, washed with acetonitrile (3 × 10 cc) and dried at 40° C. under reduced pressure (0.07 kPa). N-(7-Phenyl-1,8-naphthyridin-2-yl)-3-bromobenzamide (3.2 g), m.p. 175° C., is obtained.

2-Amino-7-phenyl-1,8-naphthyridine may be prepared by the method described by J. F. Harper, D. G. Wibberley, J. Chem. Soc. (C) 2985 (1971).

EXAMPLE 2

The procedure is analogous to that described in Example 1, but starting with 2-quinolinecarboxylic acid (10.4 g), N,N'-carbonyldiimidazole (13 g) and 2-amino-7-chloro-1,8-naphthyridine (7.2 g). After cooling at 4° C., the crystallized solid is separated by filtration, washed with distilled water (5 × 50 cc) and air-dried. The product obtained (7.4 g; m.p. 260° C.) is dissolved in a mixture of dimethylformamide (200 cc) and methanol (200 cc). After cooling for 3 hours at 4° C., the crystallized solid is separated by filtration, washed with methanol (3 × 15 cc) and dried at 35° C. under reduced pressure (0.07 kPa). N-(7-Chloro-1,8-naphthyridin-2-yl)quinoline-2-carboxamide (3.6 g), m.p. 275° C., is obtained.

EXAMPLE 3

The procedure is analogous to that described in Example 1, but starting with 3-bromobenzoic acid (6 g), N,N'-carbonyldiimidazole (4.9 g) and 2-amino-7-chloro-1,8-naphthyridine (3.6 g). The reaction mixture is poured into distilled water (100 cc) and extracted with methylene chloride (200 cc). After decanting and drying over magnesium sulphate, the solution containing methylene chloride is concentrated to dryness under reduced pressure (4 kPa) to obtain a solid (10.2 g) which is purified by chromatography on a 3-cm-diameter column containing silica (0.063–0.2 mm; 200 g), eluting with a methylene chloride/methanol (98:2 by volume) mixture. 40-cc fractions are collected. Fractions 11 to 16 are combined and concentrated to dryness under reduced pressure (4 kPa) to obtain a solid (7.1 g), m.p. 222° C.

This product is dissolved in boiling ethanol (300 cc). After cooling for 2 hours at 4° C., the crystallized solid is separated by filtration, washed with ethanol (3 × 20 cc), diethyl ether (2 × 20 cc) and dried at 40° C. under reduced pressure (4 kPa). N-(7-Chloro-1,8-naphthyridin-2-yl)-3-bromobenzamide (8.7 g), m.p. 224° C., is obtained.

EXAMPLE 4

The procedure is analogous to that described in Example 1, but starting with 3-bromobenzoic acid (6 g), N,N'-carbonyldiimidazole (4.9 g) and 2-amino-7-phenoxy-1,8-naphthyridine (5.9 g). The product obtained by precipitation in water (9.8 g; m.p. 188°–192° C.) is dissolved in acetonitrile (300 cc). After cooling for 1 hour at 4° C., the crystallized solid is separated by filtration, washed with acetonitrile (3 × 10 cc) and dried at 40° C. under reduced pressure (0.07 kPa). N-(7-Phenoxy-1,8-naphthyridin-2-yl)-3-bromobenzamide (5.4 g), m.p. 194° C., is obtained.

The 2-amino-7-phenoxy-1,8-naphthyridine may be prepared as follows:

A mixture consisting of 2-amino-7-chloro-1,8-naphthyridine (27 g), phenol (141 g) and 85% potassium hydroxide pellets (19.8 g) is heated for 20 hours at 120° C. The mixture obtained is taken up with a 4N aqueous solution of sodium hydroxide (300 cc) and extracted with methylene chloride (250 cc).

The aqueous phase is extracted again with methylene chloride (2 × 200 cc). The organic extracts are washed with 4N sodium hydroxide (2 × 150 cc) followed by distilled water (250 cc), dried over magnesium sulphate, and concentrated to dryness at 40° C. under reduced pressure (4 kPa).

The product obtained (30.5 g; m.p. 190°–194° C.) is dissolved in boiling acetonitrile (400 cc). After cooling for 2 hours at 4° C., the crystallized solid is separated by filtration, washed with acetonitrile (20 cc) and dried at 45° C., under reduced pressure (0.07 kPa). 2-Amino-7-phenoxy-1,8-naphthyridine (23.4 g), m.p. 196° C., is obtained.

EXAMPLE 5

The procedure is analogous to that described in Example 1, but starting with 3-chlorobenzoic acid (1.6 g), N,N'-carbonyldiimidazole (1.6 g) and 2-amino-7-phenyl-1,8-naphthyridine (1.6 g). The product obtained by precipitation in water (2.2 g; m.p. approximately 160° C.) is dissolved in boiling acetonitrile (200 cc). After cooling for 4 hours at 4° C., the crystallized solid is separated by filtration, washed with acetonitrile (3 × 10 cc) and dried at 40° C. under reduced pressure (0.07 kPa). N-(7-Phenyl-1,8-naphthyridin-2-yl)-3-chlorobenzamide (1.5 g), m.p. 175° C., is obtained.

The 2-amino-7-phenyl-1,8-naphthyridine may be prepared by the method described by J. F. Harper, D. G. Wibberley, J. Chem. Soc. (C), 2985 (1971).

EXAMPLE 6

The procedure is analogous to that described in Example 1, but starting with 4-trifluoromethylbenzoic acid (10 g), N,N'-carbonyldiimidazole (8.4 g) and 2-amino-7-chloro-1,8-naphthyridine (5.9 g). The product obtained by precipitation in water (11.5 g; m.p. 236° C.) is dissolved in boiling acetonitrile (250 cc). After cooling for 4 hours at 4° C., the crystallized solid is separated by filtration, washed with acetonitrile (2 × 20 cc) and dried at 45° C. under reduced pressure (0.07 kPa). N-(7-Chloro-1,8-naphthyridin-2-yl)-4-trifluoromethylbenzamide (9 g), m.p. 236° C., is obtained.

EXAMPLE 7

The procedure is analogous to that described in Example 11, but starting with 4-trifluoromethylbenzoic acid (2.7 g), N,N'-carbonyldiimidazole (2.3 g) and 2- amino-7-(4-fluorophenyl)-1,8-naphthyridine (2.4 g). The product obtained by precipitation in water (2.1 g) is dissolved in boiling methanol (50 cc). After cooling for 2 hours at 4° C., the crystallized solid is separated by filtration, washed with methanol (3×5 cc) and dried at 40° C. under reduced pressure (0.07 kPa). N-[7-(4-Fluorophenyl)-1,8-naphthyridin-2-yl]-4-trifluoromethylbenzamide (1.3 g), m.p. 198° C., is obtained.

The 2-amino-7-(4-fluorophenyl)-1,8-naphthyridine may be prepared as follows:

The procedure is analogous to that described in Example 11 below, but starting with sodium (2.3 g), 4-fluoroacetophenone (13.8 g) and ethyl formate (11 g). The solid obtained (17.8 g) is then added to 2,6-diaminopyridine (11 g). The product obtained after hydrolysis and neutralization with sodium hydroxide is separated by filtration, washed with distilled water (6×100 cc) and air-dried. 2-Amino-7-(4-fluorophenyl)-1,8-naphthyridine (17.8 g), m.p. 175° C., is thus obtained.

EXAMPLE 8

The procedure is analogous to that described in Example 1 below but starting with 4-trifluoromethylbenzoic acid (2.7 g), N,N'-carbonyldiimidazole (2.3 g) and 2-amino-7-(4-methoxyphenyl)-1,8-naphthyridine (2.5 g). The product obtained by precipitation in water (3.3 g; m.p. 144°-146° C.) is dissolved in boiling acetonitrile (100 cc). After cooling for 3 hours at 4° C., the crystallized solid is separated by filtration, washed with acetonitrile (2×10 cc) and dried at 40° C. under reduced pressure (0.07 kPa). N-[7-(4-Methoxyphenyl)-1,8-naphthyridin-2-yl]-4-trifluoromethylbenzamide (2.4 g), m.p. 148° C., is obtained.

EXAMPLE 9

Phosphoryl chloride (1.55 g) is added to a suspension of 2-amino-7-choro-1,8-naphthyridine (7.2 g) and potassium methyl terephthalate (4.4 g) in toluene (80 cc), in the course of 10 minutes. The reaction mixture is then heated at the reflux temperature for 5 hours. The suspension obtained is filtered, washed with toluene (3×20 cc), distilled water (3×20 cc), ethanol (3×20 cc) and dried at 50° C. under reduced pressure (0.07 kPa). The solid obtained (9 g; m.p. above 260° C.) is purified by chromatography on a 4-cm-diameter column containing silica (0.040-0.063 mm; 150 g), eluting with a methylene chloride/methanol (98:2 by volume) mixture. 50-cc fractions are collected. Fractions 21 to 72 are concentrated to dryness under reduced pressure (4 kPa) to obtain a solid (5.1 g) which is dissolved in boiling 1-propanol (1000 cc). After cooling for 3 hours at 4° C., the crystallized solid is separated by filtration, washed with 1-propanol (3×20 cc), and diethyl ether (3×20 cc), and then dried at 50° C. under reduced pressure (0.07 kPa). N-(7-Chloro-1,8-naphthyridin-2-yl)-4-methoxycarbonylbenzamide (4.3 g), m.p. 275° C., is obtained.

The potassium methyl terephthalate may be prepared by the method described by B. W. Hotten, Ind. Eng. Chem., Int. Ed. 49, 1691 (1957).

EXAMPLE 10

The procedure is analogous to that described in Example 1, but starting with 4-dimethylaminobenzoic acid (14.9 g), N,N'-carbonyldiimidazole (14.6 g) and 2-amino-7-chloro-1,8-naphthyridine (10.8 g). The crude product obtained by filtration of the reaction mixture (6.4 g; m.p. 248° C.) is dissolved in boiling dimethylformamide (95 cc). After cooling for 2 hours at 20° C., water (95 cc) is added. The crystallized solid is separated by filtration, washed with a dimethylformamide/water (50:50 by volume) mixture (2×10 cc), and dried at 45° C. under reduced pressure (0.07 kPa). N-(7-Chloro-1,8-naphthyridin-2-yl)-4-dimethylaminobenzamide (6.2 g), m.p. 248° C., is obtained.

EXAMPLE 11

N,N'-Carbonyldiimidazole (3.2 g) is added to a solution of 4-dimethylaminobenzoic acid (3.3 g) in anhydrous tetrahydrofuran (60 cc). Gas is evolved immediately. The mixture is stirred for 2 hours at 20° C., until the evolution of gas is complete. 2-Amino-7-(4-methoxyphenyl)-1,8-naphthyridine (3.8 g) is then added and the mixture is heated at the reflux temperature for 20 hours. The mixture is poured into distilled water (500 cc). The precipitate formed is separated by filtration, washed with water and air-dried.

The product obtained (3 g; m.p. approximately 270° C.) is dissolved in a mixture of dimethylformamide (150 cc) and acetonitrile (100 cc). After cooling for 4 hours at 4° C., the crystallized solid is separated by filtration, washed with acetonitrile (3×10 cc), and dried at 40° C. under reduced pressure (0.07 kPa). N-[7-(4-Methoxyphenyl-1,8-naphthyridin-2-yl]-4-dimethylaminobenzamide (1.2 g), m.p. 275° C., is obtained.

The 2-amino-7-(4-methoxyphenyl)-1,8-naphthyridine may be prepared as follows:

A mixture of 4-methoxy-acetophenone (15 g) and ethyl formate (11 g) is poured into a suspension of small pieces of sodium (2.3 g) in anhydrous toluene (600 cc). The reaction mixture is maintained at a temperature in the vicinity of 25° C., and stirred for 20 hours. Isopropyl ether (200 cc) is added to the suspension obtained.

The solid (17.5 g) obtained by filtering and air-drying, is added to a solution of 2,6-diaminopyridine (10.4 g) in phosphoric acid (d=1.70; 180 cc) in the course of 30 minutes. The reaction mixture is heated at 85° C. for 2 hours, stirred for 20 hours at a temperature in the vicinity of 25° C., and then poured into a mixture of distilled water (1000 cc) and ice (500 g). The precipitate formed after neutralization with 10N sodium hydroxide is separated by filtration, washed with distilled water (5×150 cc), and air-dried.

The product obtained (13 g, m.p. approximately 190° C.) is dissolved in a mixture of dimethylformamide (100 cc) and acetonitrile (100 cc). After cooling for 3 hours at 4° C., the crystallized solid is separated by filtration, washed with acetonitrile (3×15 cc) and air-dried. 2-Amino-7-(4-methoxyphenyl)-1,8-naphthyridine (5.4 g), m.p. 220° C., is obtained.

EXAMPLE 12

The procedure is analogous to that described in Example 1, but starting with 3,4-dichlorobenzoic acid (15.3 g), N,N'-carbonyldiimidazole (12.9 g) and 2-amino-7-chloro-1,8-naphthyridine (8.9 g). The product obtained by precipitation in water (17.6 g; m.p. 228° C.) is dissolved in boiling ethanol (900 cc). After cooling for 2 hours at 4° C., the crystallized solid is separated by filtration, washed with isopropyl ether (2×30 cc) and dried at 40° C. under reduced pressure (0.07 kPa). N-(7-Chloro-1,8-naphthyridin-2-yl)-3,4-dichlorobenzamide (9.2 g), m.p. 230° C., is obtained.

EXAMPLE 13

The procedure is analogous to that described in Example 1, but starting with 3,4,5-trimethoxybenzoic acid (17 g), N,N'-carbonyldiimidazole (13 g) and 2-amino-7-chloro-1,8-naphthyridine (8.9 g). The product obtained by precipitation in water (10.3 g; m.p. 90° C.) is dissolved in boiling ethanol (500 cc). After cooling for 4 hours at 4° C., the crystallized solid is separated by filtration, washed with ethanol (20 cc) and dried at 40° C. under reduced pressure (0.07 kPa). N-(7-Chloro-1,8-naphthyridin-2-yl)-3,4,5-trimethoxybenzamide (8.2 g), m.p. 210° C., is obtained.

EXAMPLE 14

The procedure is analogous to that described in Example 1, but starting with phenylacetic acid (10.9 g), N,N'-carbonyldiimidazole (13 g) and 2-amino-7-chloro-1,8-naphthyridine (10.8 g). The product obtained by precipitation in water (13.5 g; m.p. 184° C.) is dissolved in boiling acetonitrile (210 cc). After cooling for 1 hour at 4° C., the crystallized solid is separated by filtration, washed with acetonitrile (10 cc) and dried at 45° C. under reduced pressure (0.07 kPa). N-(7-Chloro-1,8-naphthyridin-2-yl)phenylacetamide (11.3 g), m.p. 187° C., is obtained.

EXAMPLE 15

Cinnamoyl chloride (7.3 g) is added to a suspension of 2-amino-7-chloro-1,8-naphthyridine (7.2 g) in pyridine (80 cc). After stirred for 2 hours at 20° C., the suspension obtained is poured into distilled water (500 cc). The suspension is filtered, washed with water (3×50 cc) and dried at 50° C. under reduced pressure (0.07 kPa). The solid obtained (10.6 g; m.p. 263° C.) is dissolved in boiling 1-propanol (1200 cc). After cooling for 4 hours at 4° C., the crystallized solid is separated by filtration, washed with 1-propanol (3×50 cc), diethyl ether (2×50 cc) and dried at 50° C. under reduced pressure (0.07 kPa). N-(7-Chloro-1,8-naphthyridin-2-yl)-3-phenylpropenamide (11.4 g), m.p. 263° C., is obtained.

EXAMPLE 16

The procedure is analogous to that described in Example 1, but starting with phenylglyoxylic acid (22.5 g), N,N'-carbonyldiimidazole (32.4 g) and 2-amino-7-chloro-1,8-naphthyridine (18 g). After cooling the reaction mixture, the crystallized solid is separated by filtration, washed with distilled water (5×100 cc), followed by ethyl ether (2×50 cc), and air-dried. The product obtained (14.4 g; m.p. greater than 250° C.) is dissolved in a mixture of dimethylformamide (100 cc) and methanol (300 cc). After cooling for 1 hour at 4° C., the crystallized solid is separated by filtration, washed with methanol (3×50 cc) and dried at 40° C. under reduced pressure (0.07 kPa). 2-Chloro-7-phenylglyoxyloylamino-1,8-naphthyridine (10.7 g), m.p. 273°–275° C., is obtained.

EXAMPLE 17

Phenyl isocyanate (15.5 g) is added to a solution of 2-amino-7-chloro-1,8-naphthyridine (17.9 g) in anhydrous tetrahydrofuran (600 cc) and the mixture is heated for 15 hours at approximately 60° C. After cooling the mixture, the crystallized solid is separated by filtration, washed with ethyl ether (3×50 cc) and air-dried. A crude product (25.2 g), m.p. 270° C., is obtained. This product (15 g) is purified under the following conditions: the product is dissolved in a mixture of dimethylformamide (200 cc) and acetonitrile (125 cc). After cooling for 5 hours at 20° C., the crystallized solid is separated by filtration, washed with acetonitrile (3×50 cc) and dried at 40° C. under reduced pressure (0.07 kPa). N-(7-Chloro-1,8-naphthyridin-2-yl)-N'-phenylurea (10.1 g), m.p. 276° C., is obtained.

EXAMPLE 18

Phenyl isocyanate (0.7 g) is added to a solution of 2-amino-7-(3-bromophenyl)-1,8-naphthyridine (1.5 g) in anhydrous tetrahydrofuran (45 cc) and the mixture is heated for 15 hours at approximately 60° C. After cooling the mixture, the crystallized solid is separated by filtration, washed with diethyl ether (3×10 cc) and air-dried. A crude product (1.1 g), m.p. approximately 260° C., is obtained.

The product is dissolved in a boiling mixture of dimethylformamide (100 cc) and acetonitrile (100 cc). After cooling for 3 hours at 20° C., the crystallized solid is separated by filtration, washed with acetonitrile (3×10 cc) and dried at 40° C. under reduced pressure (0.07 kPa). N-[7-(3-Bromophenyl)-1,8-naphthyridin-2-yl]-N'-phenylurea (0.8 g), m.p. 285° C., is obtained.

EXAMPLE 19

The procedure is analogous to that described in Example 1, but starting with benzoic acid (12.6 g), N,N'-carbonyldiimidazole (7.45 g) and 2-amino-7-(4-chlorophenoxy)-1,8-naphthyridine (12.6 g). The product obtained by precipitation in water (13 g; m.p. 100° C.) is purified by chromatography on a 4-cm-diameter column containing silica (0.040–0.063 mm; 200 g), eluting with methylene chloride and collecting 100-cc fractions. The fractions 10 to 25 are concentrated to 9/10 of the initial volume. After cooling for 2 hours at 0° C., the crystallized solid is separated by filtration, washed with diethyl ether (2×5 cc) and dried at 40° C. under reduced pressure (0.07 kPa). N-[7-(4-chlorophenoxy)-1,8-naphthyridin-2-yl]benzamide (4 g), m.p. 148° C., is obtained.

The 2-amino-7-(4-chlorophenoxy)-1,8-naphthyridine may be prepared as follows:

A mixture consisting of 2-amino-7-chloro-1,8-naphthyridine (1.8 g), 4-chlorophenol (12.85 g) and 85% strength potassium hydroxide pellets (1.1 g) is heated for 8 hours at 140° C. The reaction mixture is poured into distilled water (200 cc) and made alkaline to a pH of 10 with 4N sodium hydroxide. The suspension obtained is filtered and washed with distilled water to a pH of approximately 7. The solid obtained is air-dried to give 2-amino-7-(4-chlorophenoxy)-1,8-naphthyridine (2 g), m.p. 177° C.

EXAMPLE 20

The procedure is analogous to that described in Example 1, but starting with benzoic acid (6.5 g), N,N'-carbonyldiimidazole (8.6 g) and 2-amino-7-(1-pyrrolidinyl)-1,8-naphthyridine (8.6 g). The product obtained by precipitation in water (13 g; m.p. 110° C.) is dissolved in boiling acetonitrile (85 cc). After cooling for 2 hours at 4° C., the crystallized solid is separated by filtration, washed with acetonitrile (15 cc) and dried at 40° C. under reduced pressure (0.07 kPa). N-[7-(1-Pyrrolidinyl)-1,8-naphthyridin-2-yl]benzamide (11.5 g), m.p. 130° C., is obtained.

The 2-amino-7-(1-pyrrolidinyl)-1,8-naphthyridine may be prepared as follows:

A mixture of 2-amino-7-chloronaphthyridine (36 g) and pyrrolidine (250 cc) is heated for 2 hours at 90° C. The suspension obtained is filtered, and washed with diethyl ether (150 cc) followed by water (4×100 cc). 11 g of the solid obtained after air-drying (37 g; m.p. 249° C.) is dissolved in boiling acetonitrile (550 cc). After cooling for 1 hour at 4° C., the crystallized solid is separated by filtration, washed with acetonitrile (20 cc) and dried at 40° C. under reduced pressure (0.07 kPa). 2-Amino-7-(1-pyrrolidinyl)-1,8-naphthyridine (8.3 g), m.p. 251° C., is obtained.

EXAMPLE 21

The procedure is analogous to that described in Example 24, but starting with 2-amino-7-(2-chlorophenyl)-1,8-naphthyridine (2 g) and benzoic anhydride (4 g). The product obtained after precipitation with ethyl ether (1.2 g; m.p. 153°-155° C.) is dissolved in boiling acetonitrile (30 cc). After cooling for 2 hours at 4° C., the crystallized solvent is separated by filtration, washed with acetonitrile (2×2 cc) and dried at 40° C. under reduced pressure (0.07 kPa). N-[7-(2-Chlorophenyl)-1,8-naphthyridin-2-yl]benzamide (0.8 g), m.p. 156° C., is obtained.

The 2-amino-7-(2-chlorophenyl)-1,8-naphthyridine may be prepared as follows:

The procedure is analgous to that described in Example 11, but starting with sodium (2.3 g), 2-chloroacetophenone (15 g) and ethyl formate (11 g). The solid obtained (20 g) is then added to 2,6-diaminopyridine (11 g). The product obtained after hydrolysis and neutralization with sodium hydroxide (21.5 g; m.p. approximately 165° C.) is dissolved in concentrated hydrochloric acid (d=1.19; 100 cc). The precipitate obtained after hydrolysis with distilled water (500 cc) is separated by filtration, washed with 0.5M sodium hydroxide (3×100 cc) followed by distilled water (5×50 cc) and air-dried. 2-Amino-7-(2-chlorophenyl)naphthyridine (11 g), m.p. 193° C., is obtained.

EXAMPLE 22

The procedure is analogous to that described in Example 24 below, but starting with 2-amino-7-(4-chlorophenyl)-1,8-naphthyridine (1 g) and benzoic anhydride (2.2 g). The product obtained after precipitation with ethyl ether (1.1 g; m.p. approximately 100° C.) is purified by chromatography on a 30-mm-diameter column containing silica (0.04–0.06 mm; 50 g), eluting with methylene chloride and collecting 15-cc fractions. After concentration to dryness of fractions 12 to 28 at 40° C. under reduced pressure (4 kPa), a solid (0.6 g), m.p. 155° C., is obtained. This product is dissolved in boiling isopropanol (3 cc). After cooling for 2 hours at 4° C., the crystallized solid is separated by filtration, washed with isopropanol (0.5 cc) and dried at 40° C. under reduced pressure (0.07 kPa). N-[7-(4-Chlorophenyl)-1,8-naphthyridin-2-yl]benzamide (0.5 g), m.p. 156°-158° C., is obtained.

The 2-amino-7-(4-chlorophenyl)-1,8-naphthyridine may be prepared as follows:

The procedure is analogous to that described in Example 11, but starting with sodium (2.3 g), 4-chloroacetophenone (15.5 g) and ethyl formate (11 g). The solid obtained (20.4 g) is then added to 2,6-diaminopyridine (11.6 g). The product obtained after hydrolysis and neutralization with sodium hydroxide is separated by filtration, washed with distilled water (6×100 cc) at a temperature in the vicinity of 50° C., and then air-dried. 2-Amino-7-(4-chlorophenyl)-1,8-naphthyridine (22.6 g), m.p. approximately 130° C., is thus obtained.

EXAMPLE 23

The procedure is analogous to that described in Example 24, but starting with 2-amino-7-(3-bromophenyl)-1,8-naphthyridine (1 g) and benzoic anhydride (2.2 g). The product obtained by precipitation with ethyl ether (1.2 g; m.p. approximately 110° C.) is purified by chromatography on a 30-mm-diameter column containing silica (0.04–0.06 mm; 50 g), eluting with methylene chloride, collecting 20-cc fractions. After concentration to dryness of fractions 15 to 32 at 40° C. under reduced pressure (4 kPa), a solid (0.7 g), m.p. 202°-204° C., is obtained. This product is dissolved in boiling methylene chloride (3 cc). After cooling for 2 hours at 4° C., the crystallized solid is separated by filtration, washed with methylene chloride (0.5 cc) and dried at 40° C. under reduced pressure (0.07 kPa). N-[7-(3-bromophenyl)-1,8-naphthyridin-2-yl]benzamide (0.5 g), m.p. 204°-206° C., is obtained.

The 2-amino-7-(3-bromophenyl)naphthyridine may be prepared as follows:

The procedure is analogous to that described in Example 11, but starting with sodium (2.3 g), 3-bromoacetophenone (20 g) and ethyl formate (11 g). The product obtained (25 g) is then added to 2,6-diaminopyridine (11.6 g). The product obtained after hydrolysis and neutralization with sodium hydroxide (8.6 g; m.p. 160° C.) is dissolved in concentrated hydrochloric acid (d=1.19; 100 cc), precipitated with distilled water (400 cc), separated by filtration, washed with distilled water (6×40 cc) and air-dried.

2-Amino-7-(3-bromophenyl)-1,8-naphthyridine (6.2 g), m.p. 165°-166° C., is obtained.

EXAMPLE 24

2-Amino-7-(4-methoxyphenyl)-1,8-naphthyridine (0.8 g) is added to benzoic anhydride (2 g). The reaction mixture is heated for 30 minutes at 140° C. After cooling to 25° C., ethyl ether (15 cc) is added. The precipitate formed is separated by filtration, washed with ethyl ether (3×5 cc) and air-dried.

The product obtained (1.2 g; m.p. approximately 140° C.) is purified by chromatography on a 30-mm-diameter column containing silica (0.04–0.06 mm, 40 g), eluting with methylene chloride and collecting 15-cc fractions. After concentration to dryness of fractions 10 to 25 at 40° C. under reduced pressure (4 kPa), a solid (0.6 g), m.p. 185° C., is obtained. This product is dissolved in boiling acetonitrile (6 cc). After cooling for 2 hours at 4° C., the crystallized solid is separated by filtration, washed with acetonitrile (2×0.5 cc) and dried at 40° C. under reduced pressure (0.07 kPa). N-[7-(4-Methoxyphenyl)-1,8-naphthyridin-2-yl]benzamide (0.45 g), m.p. 185°-187° C., is obtained.

EXAMPLE 25

The procedure is analogous to that described in Example 24, but starting with 2-amino-7-(3,4-dichlorophenyl)-1,8-naphthyridine (2.5 g) and benzoic anhydride (6 g). The product obtained by precipitation with ethyl ether (1.8 g; m.p. approximately 100° C.) is dissolved in boiling acetonitrile (25 cc). The crystallized product obtained after cooling is separated by filtration, dissolved in a boiling mixture of ethanol (2 cc) and acetonitrile (5 cc). After cooling for 3 hours at 4° C., the crystallized solid is separated by filtration, washed with acetonitrile (2×1 cc) and dried at 40° C. under reduced pressure (0.07 kPa). N-[7-(3,4-Dichlorophenyl)-1,8-naphthyridin-2-yl]benzamide (0.55 g), m.p. approximately 110° C., followed by 205° C., is obtained.

The 2-amino-7-(3,4-dichlorophenyl)-1,8-naphthyridine may be prepared as follows:

The procedure is analogous to that described in Example 11, but starting with sodium (2.3 g), 3,4-dichloroacetophenone (19 g) and ethyl formate (11 g). The solid then obtained (22.7 g) is added to 2,6-diaminopyridine (11.6 g). The product obtained after hydrolysis and neutralization with 10N sodium hydroxide (22.4 g; m.p. approximately 140° C.) is dissolved in concentrated hydrochloric acid (d=1.19; 200 cc). The precipitate obtained after hydrolysis with distilled water (300 cc) followed by neutralization with 10N sodium hydroxide, is separated by filtration, washed with distilled water (5×50 cc) and air-dried. 2-Amino-7-(3,4-dichlorophenyl)-1,8-naphthyridine (14.6 g), m.p. 210° C., is obtained.

EXAMPLE 26

The procedure is analogous to that described in Example 1, but starting with 4-methoxybenzoic acid (7.6 g), N,N'-carbonyldiimidazole (9.7 g) and 2-amino-7-phenyl-1,8-naphthyridine (13.3 g). The reaction mixture is poured into distilled water (400 cc) and extracted with ethyl acetate (2×200 cc). After washing with water and drying over magnesium sulphate, the organic extracts are concentrated to dryness under reduced pressure (4 kPa) to obtain a thick oil (14.5 g). The oil obtained is purified by chromatography on a 4.2-cm-diameter column containing silica (0.040–0.063 mm; 300 g), eluting with methylene chloride. 100-cc fractions are collected; fractions 12 to 25 are concentrated to dryness under reduced pressure (4 kPa) to obtain a solid (13.4 g), m.p. about 60° C., which is dissolved in boiling ethyl acetate (425 cc). After cooling for 2 hours at 4° C., the solid obtained is separated by filtration, washed with ethyl acetate (2×15 cc) and dried at 40° C. under reduced pressure (0.07 kPa). N-(7-Phenyl-1,8-naphthyridin-2-yl)-4-methoxybenzamide (7.5 g), m.p. 187° C., is obtained.

The amino-7-phenyl-1,8-naphthyridine may be prepared according to the method described by J. F. Harper and D. G. Wibberley, J. Chem. Soc. (C) 2985 (1971).

EXAMPLE 27

The procedure is analogous to that described in Example 1, but starting with 4-methoxybenzoic acid (6.1 g), N,N'-carbonyldiimidazole (6.5 g) and 2-amino-7-anilino-1,8-naphthyridine (7 g). The product obtained by precipitation in water (12 g) is dissolved in boiling ethanol (140 cc). After cooling for 1 hour at 4° C., the crystallized solid is separated by filtration, washed with ethanol (10 cc), and dried at 45° C. under reduced pressure (0.07 kPa). N-(7-Anilino-1,8-naphthyridin-2-yl)-4-methoxybenzamide (4.5 g), m.p. 245° C., is obtained.

The 2-amino-7-anilino-1,8-naphthyridine may be obtained as follows:

A suspension of 2-amino-7-chloro-1,8-naphthyridine (9 g) in aniline (19.6 g) is heated for 19 hours at 120° C. The suspension obtained is filtered, washed with diethyl ether (3×15 cc) and air-dried. The crude solid obtained (14 g; m.p. 190° C.) is then dissolved in boiling ethanol (700 cc). After cooling for 2 hours at 4° C., the crystallized product is separated by filtration, washed with ethanol (25 cc) and air-dried. 2-Amino-7-anilino-1,8-naphthyridine (7.2 g), m.p. approximately 250° C., is obtained.

EXAMPLE 28

The procedure is analogous to that described in Example 11, but starting with 3-bromobenzoic acid (2.8 g), N,N'-carbonyldiimidazole (2.3 g) and 2-amino-7-(3-fluorophenyl)-1,8-naphthyridine (2.4 g). The product obtained by precipitation in water (3.5 g; m.p. approximately 195° C.) is dissolved in a boiling mixture of dimethylformamide (20 cc) and acetonitrile (200 cc). After cooling for 4 hours at 4° C., the crystallized solid is separated by filtration, washed with acetonitrile (3×10 cc) and dried at 40° C. under reduced pressure (0.07 kPa). N-[7-(3-Fluorophenyl)-1,8-naphthyridin-2-yl]-3-bromobenzamide (2.3 g), m.p. 208° C., is obtained.

The 2-amino-7-(3-fluorophenyl)-1,8-naphthyridine may be prepared as follows:

The procedure is analogous to that described in Example 11, but starting with sodium (2.5 g), 3-fluoroacetophenone (15 g) and ethyl formate (12.6 g). The solid obtained (18.8 g) is then added to 2,6-diaminopyridine (12.1 g). The product obtained after hydrolysis and neutralization with sodium hydroxide (22 g; m.p. approximately 140° C.) is dissolved in dimethylformamide (250 cc). The product obtained by precipitation in water is separated by filtration, washed with distilled water (2×100 cc) and air-dried.

2-Amino-7-(3-fluorophenyl)-1,8-naphthyridine (14.8 g), m.p. 160° C., is obtained.

EXAMPLE 29

The procedure is analogous to that described in Example 11, but starting with 3-bromobenzoic acid (2.1 g), N,N'-carbonyldiimidazole (1.6 g) and 2-amino-7-(4-fluorophenyl)-1,8-naphthyridine (1.7 g). The product obtained by precipitation in water (2 g) is dissolved in boiling propanol (200 cc). After cooling for 4 hours at 4° C., the crystallized solid is separated by filtration, washed with propanol (3×10 cc) and dried at 40° C. under reduced pressure (0.07 kPa). N-[7-(4-Fluorophenyl)-1,8-naphthyridin-2-yl]-3-bromobenzamide (1.4 g), m.p. 210° C., is obtained.

EXAMPLE 30

The procedure is analogous to that described in Example 11, but starting with 3-chlorobenzoic acid (1.6 g), N,N'-carbonyldiimidazole (1.6 g) and 2-amino-7-(4-chlorophenyl)-1,8-naphthyridine (1.8 g). The product obtained by precipitation in water (2.2 g; m.p. approximately 190° C.) is dissolved in boiling propanol (400 cc). After cooling for 4 hours at 4° C., the crystallized solid is separated by filtration, washed with propanol (3×5 cc) and dried at 40° C. under reduced pressure (0.07 kPa). N-[7-(4-Chlorophenyl)-1,8-naphthyridin-2-yl]-3-chlorobenzamide (0.85 g), m.p. 222°–224° C., is obtained.

EXAMPLE 31

The procedure is analogous to that described in Example 11, but starting with 3-bromobenzoic acid (2.1 g), N,N'-carbonyldiimidazole (1.6 g) and 2-amino-7-(4-chlorophenyl)-1,8-naphthyridine (1.8 g). The product obtained by precipitation in water (2.2 g; m.p. 210° C.) is dissolved in a boiling mixture of dimethylformamide (20 cc) and acetonitrile (100 cc). After cooling for 4 hours at 4° C., the crystallized solid is separated by filtration, washed with acetonitrile (3×10 cc) and dried at 40° C. under reduced pressure (0.07 kPa). N-[7-(4-Chlorophenyl)1,8-naphthyridin-2-yl]-3-bromobenzamide (1.4 g), m.p. 220°-224° C., is obtained.

EXAMPLE 32

The procedure is analogous to that described in Example 11, but starting with 3-bromobenzoic acid (2.2 g), N,N'-carbonyldiimidazole (1.8 g) and 2-amino-7-(3-bromophenyl)-1,8-naphthyridine (2.4 g). The product obtained by precipitation in water (3.1 g; m.p. approximately 140° C.) is dissolved in boiling propanol (100 cc). After cooling for 3 hours at 4° C., the crystallized solid is separated by filtration, washed with propanol (2×10 cc) and dried at 40° C. under reduced pressure (0.07 kPa). N-[7-(3-Bromophenyl)-1,8-naphthyridin-2-yl]-3-bromobenzamide (2.2 g), m.p. 144°-146° C., is obtained.

EXAMPLE 33

The procedure is analogous to that described in Example 11, but starting with 3-bromobenzoic acid (1.6 g), N,N'-carbonyldiimidazole (1.3 g) and 2-amino(2-methoxyphenyl)-1,8-naphthyridine (1.3 g). The product obtained by precipitation in water (1.5 g) is dissolved in boiling methanol (75 cc). After cooling for 2 hours at 4° C., the crystallized solid is separated by filtration, washed with methanol (3×3 cc) and dried at 35° C. under reduced pressure (0.07 kPa). N-[7-(2-Methoxyphenyl)-1,8-naphthyridin-2-yl]-3-bromobenzamide (0.6 g), m.p. 110° C., is obtained.

The 2-amino-7-(2-methoxyphenyl)-1,8-naphthyridine may be prepared as follows:

The procedure is analogous to that described in Example 11, but starting with sodium (2.3 g), 2-methoxyacetophenone (15 g) and ethyl formate (11 g). The solid obtained (19.8 g) is then added to 2,6-diaminopyridine (11.6 g). The product obtained after hydrolysis and neutralization with sodium hydroxide (10.9 g; m.p. approximately 145° C.) is dissolved in dichloromethane (200 cc) and crystallized by adding a 3N solution (15 cc) of hydrochloric acid in ethyl ether. The crystallized product is separated by filtration, washed with dichloromethane (3×20 cc), followed by acetonitrile (3×10 cc) and dissolved in distilled water (60 cc). The precipitate obtained after neutralization with a saturated aqueous solution of sodium bicarbonate is separated by filtration, washed with distilled water (5×15 cc), and air-dried. 2-Amino-7-(2-methoxyphenyl)-1,8-naphthyridine (2.9 g), m.p. 182° C., is obtained.

EXAMPLE 34

The procedure is analogous to that described in Example 11, but starting with 3-bromobenzoic acid (4 g), N,N'-carbonyldiimidazole (3.2 g) and 2-amino-7-(3-methoxyphenyl)-1,8-naphthyridine (3.5 g). The product obtained by precipitation in water (4 g; m.p. approximately 90° C.) is dissolved in boiling acetonitrile (200 cc). After cooling for 3 hours at 4° C., the crystallized solid is separated by filtration, washed with acetonitrile (3×3 cc) and dried at 35° C. under reduced pressure (0.07 kPa). N-[7-(3-Methoxyphenyl)-1,8-naphthyridin-2-yl]-3-bromobenzamide (0.8 g), m.p. 104° C., is obtained.

The 2-amino-7-(3-methoxyphenyl)-1,8-naphthyridine may be prepared as follows:

The procedure is analogous to that described in Example 11, but starting with sodium (2.3 g), 3-methoxyacetophenone (15 g) and ethyl formate (11 g). The solid obtained (20 g) is then added to 2,6-diaminopyridine (11 g). The product obtained after hydrolysis and neutralization with sodium hydroxide is separated by filtration, washed with distilled water (6×100 cc) at 50° C., and then air-dried. 2-Amino-7-(3-methoxyphenyl)-1,8-naphthyridine (23.8 g), m.p. 270°-275° C., is obtained.

EXAMPLE 35

The procedure is analogous to that described in Example 11, but starting with 3-bromobenzoic acid (2.8 g), N,N'-carbonyldiimidazole (2.3 g) and 2-amino-7-(3-methylphenyl)-1,8-naphthyridine (2.4 g). The product obtained by precipitation in water (2.3 g) is dissolved in boiling acetonitrile (300 cc). After 4 hours of cooling at 4° C., the crystallized solid is separated by filtration, washed with acetonitrile (3×5 cc) and dried at 35° C. under reduced pressure (0.07 kPa). N-[7-(3-Methylphenyl)-1,8-naphthyridin-2-yl]-3-bromobenzamide (1 g), m.p. 100° C., is obtained.

The 2-amino-7-(3-methylphenyl)-1,8-naphthyridine may be prepared as follows:

The procedure is analogous to that described in Example 11, but starting with sodium (2.3 g), 3-methylacetophenone (13.4 g) and ethyl formate (11 g). The solid obtained (18.4 g) is then added to 2,6-diaminopyridine (12.1 g). The product obtained after hydrolysis and neutralization with sodium hydroxide (14 g); m.p. approximately 140° C.) is dissolved in concentrated hydrochloric acid (d=1.19; 100 cc). The precipitate obtained after hydrolysis with distilled water (500 cc) followed by neutralization with 10N sodium hydroxide is separated by filtration, washed with distilled water (5×50 cc) and methanol (2×50 cc), and then air-dried. 2-Amino-7-(3-methylphenyl)-1,8-naphthyridine (7.3 g), m.p. 180° C., is obtained.

EXAMPLE 36

The procedure is analogous to that described in Example 11, but starting with 3-bromobenzoic acid (2.1 g), N,N'-carbonyldiimidazole (1.6 g) and 2-amino-7-(3,4-dichlorophenyl)-1,8-naphthyridine (2.1 g). The product obtained by precipitation in water (2.5 g; m.p. approximately 150° C.) is dissolved in a boiling mixture of dimethylformamide (75 cc) and acetonitrile (100 cc). After cooling for 4 hours at 4° C., the crystallized solid is separated by filtration, washed with acetonitrile (3×5 cc) and dried at 40° C. under reduced pressure (0.07 kPa).

N-[7-(3,4-Dichlorophenyl)-1,8-naphthyridin-2-yl]-3-bromobenzamide (1.2 g), m.p. 176°-178° C., is obtained.

The present invention also provides pharmaceutical compositions containing an amide of formula (I) in combination with a compatible, pharmaceutically acceptable adjuvant, diluent and/or coating. Thse pharmaceutical compositions may be administered by the oral, rectal, parenteral, percutaneous or intranasal route.

As solid compositions for oral administration, tablets, pills, powders (generally in gelatin capsules) or granules may be used. In these compositions, the active substance according to the invention is mixed with one or more inert diluents, such as saccharose, lactose or starch. These compositions may also contain substances other than diluents, e.g., a lubricant such as magnesium stearate.

As liquid compositions for oral administration, pharmaceutically acceptable emulsions, solutions, suspensions, syrups and elixirs containing inert diluents such as water or paraffin oil may be used. These compositions may also contain substances other than diluents, e.g., wetting, sweetening or flavouring agents.

The compositions according to the invention for intranasal or parenteral administration may be aqueous or non-aqueous sterile solutions, suspensions or emulsions. As solvent or vehicle, propylene glycol, a polyethylene glycol, vegetable oils, especially olive, almond or coconut oil, and injectable organic esters, e.g., ethyl oleate may be used. These compositions may also contain adjuvants, especially wetting agents, emulsifiers or dispersants (soybean lecithin). Sterilization may be carried out in several ways, e.g., by incorporating sterilizing agents into the compositions, by irradiation, by heating or by adding a preservative. They may be produced in the form of sterile solid compositions which will be dissolved in an injectable sterile medium at the time of use.

The compositions for rectal administration are suppositories which may contain, in addition to the active substance, excipients such as cocoa butter or suppowax.

The compositions for percutaneous administration are creams, ointments, lotions and liniments, in which the active substance is combined with liquid or pasty excipients, preferably in combination with a vehicle which promotes the percutaneous migration.

The amide of formula I and compositions containing them are especially useful in human therapeutics because of their anti-infectious and immunorestorative action.

In human therapeutics, the dosage used depends on the effect sought and the duration of the treatments. It is generally from 5 to 250 mg per day by the oral route, or from 0.5 to 25 mg per day by the parenteral route, for an adult. In general, the doctor will determine the dosage that he considers most appropriate depending on the age, weight and other factors which are specific to the subject to be treated.

The examples which follow illustrate compositions according to the invention.

EXAMPLE A

In accordance with the usual technique, tablets containing 5 mg of the active substance are prepared having the following composition:

| | |
|---|---|
| N—(7-Phenyl-1,8-naphthyridin-2-yl)-3-bromobenzamide | 0.005 g |
| Starch | 0.100 g |
| Precipitated silica | 0.018 g |
| Magnesium stearate | 0.002 g |

EXAMPLE B

In accordance with the usual technique, an injectable solution having the following composition is prepared:

| | |
|---|---|
| N—(7-Phenyl-1,8-naphthyridin-2-yl)-4-methoxybenzamide | 0.020 g |
| Propylene glycol | 1 cc |
| Water for injectable preparations q.s. | 2 cc |

EXAMPLE C

In accordance with the usual technique, tablets containing 5 mg of the active ingredient are prepared having the following composition:

| | |
|---|---|
| N—[7-(1-Pyrrolidinyl)-1,8-naphthyridin-2-yl]benzamide | 0.005 g |
| Starch | 0.100 g |
| Precipitated silica | 0.018 g |
| Magnesium stearate | 0.002 g |

We claim:

1. A substituted amide of the formula:

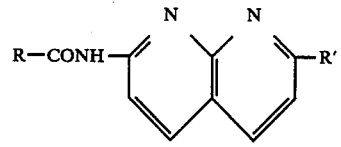

in which either:
(1) R represents 2-quinolyl, substituted phenyl (the substituent being bromine, chlorine in position -3, trifluoromethyl, alkyloxycarbonyl, or dialkylamino in position -4), dichlorophenyl, trialkyloxyphenyl, benzyl, styryl, benzoyl or anilino, and
R' represents halogen, phenyl, anilino, or R' represents phenoxy or 4-chlorophenoxy when R is 2-quinolyl, substituted phenyl (the substituent being bromine, chlorine in position -3, trifluoromethyl, alkyloxycarbonyl, or dialkylamino in position -4), trialkyloxyphenyl, benzyl or styryl, or R' represents 4-fluorophenyl or 4-alkyloxyphenyl when R is 4-trifluoromethylphenyl or 4-dialkylaminophenyl, or R' represents 3-bromophenyl when R is anilino, or
(2) R represents phenyl or alkyloxyphenyl and R' represents phenyl, 4-chlorophenoxy, anilino or 1-pyrrolidinyl, or
R' represents 2-(or 4-)chlorophenyl, 3-(or 4-)bromophenyl, 4-alkyloxyphenyl or 3,4-dichloro(or dibromo)phenyl when R is phenyl, or
(3) R represents phenyl substituted by halogen in position -3 and
R' represents 3-(or 4-)fluorophenyl, 3-(or 4-)bromophenyl, 4-chdlorophenyl, 2-(or 3-)alkyloxyphenyl, 3-alkylphenyl, or 3,4-difluoro(dichloro or dibromo)phenyl:

the aforesaid alkyl radicals being straight-chain or branched and containing 1 to 4 carbon atoms each.

2. An amide according to claim 1, wherein either:
(1) R. represents 2-quinolyl, 4-dialkylaminophenyl, dichlorophenyl, trialkyloxyphenyl, benzyl, styryl or benzoyl, and
R' represents chlorine or phenyl, or
R' represents phenoxy when R is bromophenyl, or
R' represents chlorine when R is bromophenyl, trifluoromethylphenyl or anilino, or
R' represents 3-bromophenyl when R is anilino, or (2) R represents phenyl or alkyloxyphenyl and
R' represents phenyl, 4-chlorophenoxy, anilino or 1-pyrrolidinyl, or
R' represents 2-(or 4-)chlorophenyl, 3-(or 4-)bromophenyl, or 4-alkyloxyphenyl when R is phenyl, or (3) R represents phenyl substituted in the 3-position by a halogen atom and R' represents 3-(or 4-)fluorophenyl, 3-(or 4-)bromophenyl, 4-chlorophenyl, 2-(or 3-)alkyloxyphenyl, 3-alkylphenyl or 3,4-difluoro(or dichloro or dibromo)phenyl, the aforesaid alkyl radicals being straight-chain or branched and containing 1 to 4 carbon atoms each.

3. The substituted amide according to claim 1 which is N-(7-phenyl-1,8-naphthyridin-2-yl)-3-bromobenzamide.

4. The substituted amide according to claim 1 which is N-(7-phenyl-1,8-naphthyridin-2-yl)-4-methoxybenzamide.

5. The substituted amide according to claim 1 which is N-(7-(1-pyrrolidinyl)-1,8-naphthyridin-2-yl)-benzamide.

6. The substituted amide according to claim 1 which is N-(7-(4-chlorophenyl)-1,8-naphthyridin-2-yl)-3-bromobenzamide.

7. The substituted amide according to claim 1 which is N-(7-(4-fluorophenyl)-1,8-naphthyridin-2-yl)-3-bromobenzamide.

8. A pharmaceutical composition useful as an immunostimulant comprising an effective amount of an amide according to claim 1 in combination with one or more compatible, pharmaceutically acceptable diluents or adjuvants.

* * * * *